(12) United States Patent
Tseti

(10) Patent No.: US 8,333,192 B2
(45) Date of Patent: Dec. 18, 2012

(54) DRY POWDER COMPRISING LEVOTHYROXINE SODIUM ADMINISTRATED VIA INHALATOR

(75) Inventor: Ioulia Tseti, Kifissia (GR)

(73) Assignee: Uni-Pharma Kleon Tstetis Pharmaceuticals Laboratories S.A., Kifissia (GR)

(*) Notice: Subject to any disclaimer, the term of this patent is extended or adjusted under 35 U.S.C. 154(b) by 1393 days.

(21) Appl. No.: 11/791,100

(22) PCT Filed: Nov. 18, 2004

(86) PCT No.: PCT/GR2004/000055
§ 371 (c)(1),
(2), (4) Date: Oct. 25, 2007

(87) PCT Pub. No.: WO2006/054120
PCT Pub. Date: May 26, 2006

(65) Prior Publication Data
US 2008/0178870 A1    Jul. 31, 2008

(51) Int. Cl.
*A61K 31/198* (2006.01)
(52) U.S. Cl. .................................. 128/203.15; 424/46
(58) Field of Classification Search ............. 128/203.15, 128/200.14, 200.12, 200.15, 200.17, 203.16–203.24; 424/46, 489
See application file for complete search history.

(56) References Cited

U.S. PATENT DOCUMENTS

| 5,161,524 A | 11/1992 | Evans |
| 6,553,987 B1 | 4/2003 | Davies |
| 6,646,007 B1 | 11/2003 | Schreder et al. |
| 2004/0033259 A1 | 2/2004 | Hanshew et al. |

FOREIGN PATENT DOCUMENTS

| GB | 2 240 474 | 8/1991 |
| GR | 1004350 B1 | 9/2003 |
| PL | 17876 | 1/1933 |
| WO | 89/07454 | 8/1989 |

OTHER PUBLICATIONS

Agu R U et al, "The Lung as a route for systemic delivery of therapeutic proteins and peptides" in Respiratory Research 2001 vol. 2 No. 4 2001, pp. 198-209.
PCT International Search Report of International Application GR2004/000055 filed on Nov. 18, 2004 in the name of Uni-Pharma Kleon Tsetis Pharmaceutical.
PCT International Preliminary Report on Patentability of International Application GR2004/000055 filed on Nov. 18, 2004 in the name of Uni-Pharma Kleon Tsetis Pharmaceutical.
PCT Written Opinion of International Application GR2004/000055 filed on Nov. 18, 2004 in the name of Uni-Pharma Kleon Tsetis Pharmaceutical.
Decision to grant a European patent pursuant to Article 97(1) EPC issued by the EPO on Mar. 6, 2008 for EP application 04798720.1.
Communication under Rule 51(4) EPC issued by the EPO on Oct. 25, 2007 for EP application 04798720.1.

*Primary Examiner* — Steven Douglas
(74) *Attorney, Agent, or Firm* — Steinfl & Bruno, LLP

(57) ABSTRACT

A device comprising an inhaler suitable for administration of a stable dry powder blend is described, which contains a blend comprising a thyroid hormone, in particular levothyroxine sodium, and other additives such as lactose particles, sodium starch glycolate, magnesium stearate, and talc silicified.

9 Claims, 1 Drawing Sheet

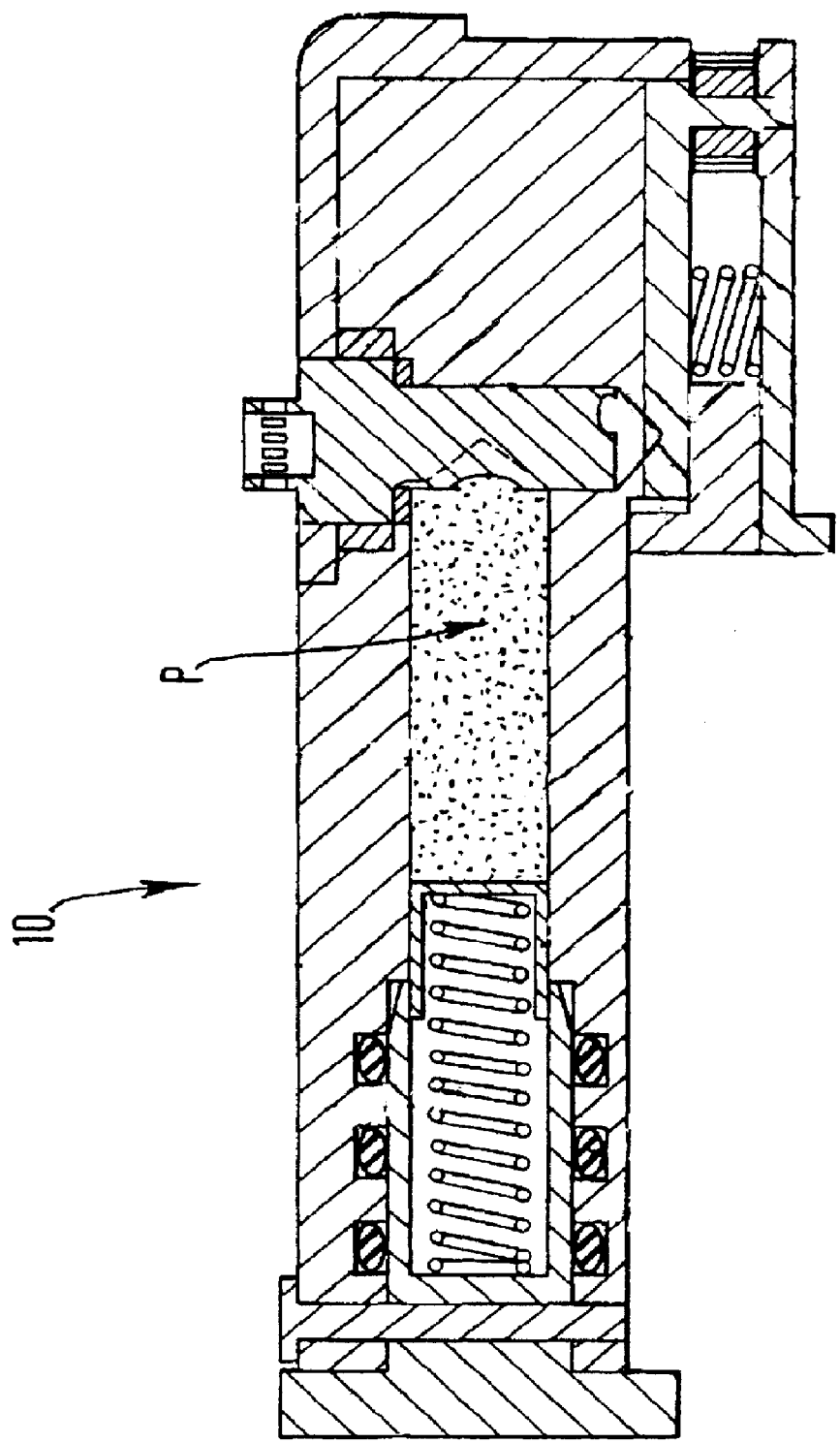

DRY POWDER COMPRISING LEVOTHYROXINE SODIUM ADMINISTRATED VIA INHALATOR

TECHNICAL FIELD

The invention relates to a new way of administration of thyroid hormone preparations by using an inhaler.

PRIOR ART

Stable thyroid hormone preparations in form of tablets are already disclosed in the prior art, e.g. in the documents U.S. Pat. No. 6,646,007 B1 and U.S. Pat. No. 0,033,259 A1.

Document U.S. Pat. No. 6,646,007 B1, herein fully incorporated by reference, discloses a process for producing a thyroid preparation comprising levothyroxine sodium, gelatine and fillers and is free of organic residues. The preparation contains 5-400 or 10-300 or 25-300 micrograms of levothyroxine sodium. Further compounds, like liothyronine sodium, lactose and/or maize starch and/or microcrystalline cellulose, can be also included. The particle size of the micronised levothyroxine sodium is 2-25 micrometers. The preparation is finally prepared in the form of tablets.

Administration of the thyroid hormones by using inhalers is not mentioned in the document U.S. Pat. No. 6,646,007 B1.

Various dry powder inhalers suitable for dry powder are already described in the prior art, e.g. see the documents U.S. Pat. No. 6,553,987, PL-B-17876, U.S. Pat. No. 5,161,524 and GR-A-1004350, all of them herein fully incorporated by reference.

The pharmaceutical powder is stored either inside (e.g. U.S. Pat. No. 6,553,987) or outside (e.g. GR-A-10043350) the housing of the inhaler.

Each one of the above inhalers optimises differently the conditions of functioning in order to get optimum (unit) dosing, high dose accuracy (by appropriate metering system), optimum powder flow, easy to operate and reproducibility of results. They can be used for administration of therapeutic agents to the lungs, throat, respiratory tract.

In particular, document U.S. Pat. No. 6,553,987, herein fully incorporated by reference, mentions the use of a specific inhaler with dry powders. Out of a long list of possible dry powders, some may comprise hormones, said hormones being cortisone, hydrocortisone, prednisolone, insulin. Thyroid hormones are not mentioned in the document U.S. Pat. No. 6,553,987.

PRESENT INVENTION

The present invention is a device comprising an inhaler, like anyone of the inhalers disclosed in the documents U.S. Pat. No. 6,553,987, PL-B-17876, U.S. Pat. No. 5,161,524 and GR-A-1004350 and a reservoir of dry powder, said dry powder comprising thyroid hormone like levothyroxine sodium, and excipient(s) like lactose.

The inhaler used in the present invention is not limited to the inhalers of said documents U.S. Pat. No. 6,553,987, PL-B-17876, U.S. Pat. No. 5,161,524 and GR-A-1004350. However, the inhaler of the document U.S. Pat. No. 6,553,987 (GSK) is one of the various preferred inhalers.

None of the prior art documents discloses the present invention, i.e. an inhaler device comprising a thyroid hormone dry powder.

Though hormones are referred in document U.S. Pat. No. 6,553,987, no-where in said document U.S. Pat. No. 6,553,987 "thyroid hormones" are mentioned.

Moreover, the thyroid hormone preparations of the past, e.g. see U.S. Pat. No. 6,646,007 B1, were suitable for administration as "tablets", not via inhalation.

Thus, the present invention relating in an "inhalator" comprising "thyroid hormone" dry powder is new.

BRIEF DESCRIPTION OF DRAWINGS

FIG. 1 is a schematic illustration of an exemplary inhaler (10) suitable for dry powder (P) already described in U.S. Pat. No. 6,553,987, herein incorporated by reference in its entirety.

By combining the stable dry powder preparation of thyroid hormone with the inhalers, all advantages mentioned in the corresponding patents documents relating in administration via said inhalers are valid (see documents U.S. Pat. No. 6,553,987, PL-B-17876, U.S. Pat. No. 5,161,524, GR-A-1004350 disclosing inhalers wherein the pharmaceutical powder is stored either inside—e.g. see document U.S. Pat. No. 6,553,987—or outside—e.g. see document GR-A-10043350—the housing of the inhaler).

Moreover, further problems of the prior art are overcome.

Thus, the patients prejudice to change from the tablet administration (à priori considered as comfortable administration) to inhalation (à priori considered as not comfortable administration), was not confirmed by practice.

Patients found that the administration of thyroid hormones by using an inhaler (accurate dose well adapted to their needs) is more comfortable than the oral-tablet administration (tablets show less accurate dose than the administration via inhaler). Moreover, the absorption of the active thyroid hormone was traditionally considered to be more efficient if done in the gastroenteric tract, i.e. when tablets via oral administration were used.

By the administration of thyroid hormones according to the present invention, i.e. via inhalation of dry powder, we were surprised to find that the absorption was significantly improved—in terms of accuracy of dose of hormone, accuracy of amount absorbed and rate of absorption—over the tablets administration (oral), since no losses of the active hormone was observed in the oral cavity and the respiratory tract and the dilution in the gastroenteric tract/stomach of the hormone was less significant than in the case of tablets.

We consider that, contrary to the prior art (referring only to "oral" administration of stable "tablets" comprising thyroid hormones), the "inhalation" of a stable "dry powder" comprising thyroid hormone optimises the absorption, through minimisation of the losses of hormone and increase of the accuracy and repeatability of the dose absorbed.

Given the importance of an optimised absorption of the thyroid hormones—wherein the losses of active are minimum and the accuracy and repeatability of the dose absorbed are improved—our invention shows a major advantage over the tablet administration of the prior art.

It is well known that the (unit) doses of thyroid hormones absorbed should be very accurate. The physicians adapt the dose administrated at regular time intervals according to the changing needs of the patients.

Contrary to the prior art, over-dosing or under-dosing are, therefore, avoided by the administration of the thyroid hormones according to the present invention.

According to the present invention, the amount of levothyroxine sodium is 4 to 0.02 mg per 100 mg of the dry powder preparation, e.g. 0.233 or 0.204 or 0.175 or 0.160 or 0.146 or 0.131 or 0.117 or 0.103 or 0.087 or 0.058 or 0.029 mg per 100 mg of dry powder preparation.

According to the present invention, the amount of lactose is higher than 90 mg per 100 mg of the dry powder preparation, e.g. 91.767 or 91.796 or 91.825 or 91.840 or 91.854 or 91.869 or 91.883 or 91.897 or 91.913 or 91.942 or 91.971 mg per 100 mg of dry powder preparation.

Preferably the lactose particles of the present invention consist of lactoseH2O, gelatine and starch maize. Preferably the mg-ratio of "lactoseH2O":"gelatine":"starch maize" is 55-75:0.20-0.80:20-40 e.g. 60.512:0.505:30.750 or 60.541:0.505:30.750 or 60.570:0.505:30.750 or 60.585:0.505:30.750 or 60.599:0.505:30.750 or 60.614:0.505:30.750 or 60.628:0.505:30.750 or 60.642:0.505:30.750 or 60.658:0.505:30.750 or 60.687:0.505:30.750 or 60.716:0.505:30.750

Moreover, the dry powder preparation of the present invention can comprise sodium starch glycolate preferably in an amount of 4-8 mg per 100 mg of dry powder preparation, more preferably 5 or 6 mg of dry powder.

Furthermore, magnesium stearate can be also comprised in the dry powder preparation of the present invention preferably in an amount of 0.5-2 more preferably 1 mg per 100 mg of dry powder preparation.

Additionally, talc silicified can be also comprised in the dry powder preparation of the present invention in an amount of 2 mg per 100 mg of dry powder preparation.

Said talc silicified preferably comprising talc purified and colloidal silicon dioxide preferably in the amount of 0.667 mg of talc purified and 1.333 mg of colloidal silicon dioxide for 2 mg of talc silicified.

The invention relates to a device comprising a stable dry powder of thyroid hormone, said device:

Item-1) comprising a metering system suitable for use in a dry powder inhaler comprising: a. a housing defining a reservoir, said reservoir containing a powder; b. a rotatable auger defining one or more spiral flutes; said auger having a first and second end and said one or more spiral flute extending therebetween, said first end in communications with said reservoir, and; c. a dosing member defining a dosing recess having a desired volume, said dosing recess positionable adjacent said second end of said auger; whereby rotation of said auger causes said powder to be transferred from said reservoir, through said flutes through said second end of said auger and into said dosing recess to fill said volume.

Item-2) Device according to item 1 wherein the auger has a circumference and the reservoir interfaces with only a portion of the circumference of the auger at the bore/reservoir interface.

Item-3) Device according to item 1 further comprising a plunger positioned within the reservoir and biased toward the auger.

Item-4) Device according to item 1 wherein the bore extends through the housing, and auger has a drive at one end facilitating rotation of the auger.

Item-5) Device according to item 1 for dosing powder in a dry powder inhaler comprising: a. an inhaler housing defining a reservoir, a bore and a bore egress, the reservoir having a first and a second end and an axis therebetween, the bore extending into the housing, and the bore and the reservoir in communication at the second end of the reservoir at a bore/reservoir interface, the bore having an axis, the axis of the bore being non-parallel and non-coaxial with the axis of the reservoir, the bore egress in communication with the bore; and b. a rotatable auger positioned coaxially within the bore, said auger suitable for delivering powder for dosation, the auger having a length, a flute at least partially spirally extending along a portion of said length, the flute allowing communication between the bore/reservoir interface and the bore egress.

Item-6) Device according to item 5, wherein the reservoir axis is approximately perpendicular to the bore axis.

Item-7) Device according to item 5, further comprising a dose plate defining a dosing recess, the dosing recess in communication with the bore egress.

Item-8) Device according to item 7, wherein the dose plate is movable between a loading position wherein the dosing recess is adjacent the bore egress, and a delivery position wherein the contents of the recess may be removed.

Item 9) Device according to item 8, wherein the dose plate is movable pivotally between the loading and delivery positions.

Item-10) Device according to item 5, wherein the bore egress comprises an intermediate chamber.

Item-11) Device according to item 10, wherein the intermediate chamber is tapers toward the dosing recess.

Item-12) Device according to item 1 further comprising a powder within the reservoir.

The invention also relates to a device comprising a stable dry powder of thyroid hormone, said device:

Item-13) comprising a dry powder inhaler apparatus having an inhaler body with an air inlet, an air outlet, and an air flow pathway therebetween, and further comprising: a. a walled portion defining a reservoir and a bore, the reservoir having a first end and a second end and an axis therebetween, the bore extending from a bore egress into the housing, and the bore and the reservoir in communication at one end of the reservoir at a bore/reservoir interface, the bore having an axis, the axis of the bore being non-parallel and non-coaxial with the axis of the reservoir; b. a rotatable auger positioned coaxially within the bore, a spiral groove defined in the auger, the groove extending between the bore/reservoir interface and the bore egress; the direction of powder transfer is non coaxial with the plane of rotation of the auger; and c. a dose plate, said dose plate defining a dosing recess, the dose plate movable between a loading position, in which the dosing recess is in communication with the bore egress, and a delivery position in which the dosing recess is in communication with the air flow pathway.

Item-14) Device according to item 13 wherein the dry powder inhaler apparatus further comprises a loading arm capable of engaging the auger to cause rotation of the auger.

Item-15) Device according to item 13 wherein the dry powder inhaler apparatus further comprises a dose plate transfer arm capable of engaging the dose plate to move the dose plate between the loading and delivery positions.

Item-16) Device according to item 13 wherein the dry powder inhaler apparatus further comprises: a. an integrated mouthpiece cover positioned within the inhaler body, the integrated mouthpiece cover having a loading arm and a dose plate transfer arm, and wherein the integrated mouthpiece cover is moveable between a closed position, in which the dose plate is in the loading position, and an open position, in which the dose plate is in the delivery position and the dosing recess is in the air flow pathway.

Item-17) Device according to item 13 wherein the bore egress comprises an intermediate chamber.

The invention is defined by the appended claims.

EXAMPLES

A) In the following examples 1-11 the dry powder compositions containing thyroid hormones are identical with the composition of the commercial tablet-products under the name T4 (trade mark of UNI-PHARMA).

Example 1

Dry powder comprising thyroid hormone (same composition as T4-200) was prepared.
Composition of 100 mg of dry powder:
Levothyroxine sodium hydrate *: 0.233 mg (5% excess)
Lactose ** (particles): 91.767 mg
Sodium Starch Glycolate: 5 mg
Magnesium Stearate: 1 mg
Talc Silicified ***: 2 mg
* Corresponds to 0.2 mg levothyroxine sodium
** Consists of:
60.512 mg lactose H2O
0.505 mg gelatine and
30.75 mg starch maize
*** Consists of:
0.667 mg talc purified
1.333 mg colloidal silicon dioxide

Example 2

Dry powder comprising thyroid hormone (same composition as T4-175) was prepared.
Composition of 100 mg of dry powder:
Levothyroxine sodium hydrate *: 0.204 mg (5% excess)
Lactose ** (particles): 91.796 mg
Sodium Starch Glycolate: 5 mg
Magnesium Stearate: 1 mg
Talc Silicified ***: 2 mg
* Corresponds to 0.175 mg levothyroxine sodium
** Consists of:
60.541 mg lactose H2O
0.505 mg gelatine and
30.75 mg starch maize
*** Consists of:
0.667 mg talc purified
1.333 mg colloidal silicon dioxide

Example 3

Dry powder comprising thyroid hormone (same composition as T4-150) was prepared.
Composition of 100 mg of dry powder:
Levothyroxine sodium hydrate *: 0.175 mg (5% excess)
Lactose ** (particles): 91.825 mg
Sodium Starch Glycolate: 5 mg
Magnesium Stearate: 1 mg
Talc Silicified ***: 2 mg
* Corresponds to 0.15 mg levothyroxine sodium
** Consists of:
60.570 mg lactose H2O
0.505 mg gelatine and
30.75 mg starch maize
*** Consists of:
0.667 mg talc purified
1.333 mg colloidal silicon dioxide

Example 4

Dry powder comprising thyroid hormone (same composition as T4-137) was prepared.
Composition of 100 mg of dry powder:
Levothyroxine sodium hydrate *: 0.160 mg (5% excess)
Lactose ** (particles): 91.840 mg
Sodium Starch Glycolate: 5 mg
Magnesium Stearate: 1 mg
Talc Silicified ***: 2 mg
* Corresponds to 0.137 mg levothyroxine sodium
** Consists of:
60.585 mg lactose H2O
0.505 mg gelatine and
30.75 mg starch maize
*** Consists of:
0.667 mg talc purified
1.333 mg colloidal silicon dioxide

Example 5

Dry powder comprising thyroid hormone (same composition as T4-125) was prepared.
Composition of 100 mg of dry powder:
Levothyroxine sodium hydrate *: 0.146 mg (5% excess)
Lactose ** (particles): 91.854 mg
Sodium Starch Glycolate: 5 mg
Magnesium Stearate: 1 mg
Talc Silicified ***: 2 mg
* Corresponds to 0.125 mg levothyroxine sodium
** Consists of:
60.599 mg lactose H2O
0.505 mg gelatine and
30.75 mg starch maize
*** Consists of:
0.667 mg talc purified
1.333 mg colloidal silicon dioxide

Example 6

Dry powder comprising thyroid hormone (same composition as T4-112) was prepared.
Composition of 100 mg of dry powder:
Levothyroxine sodium hydrate *: 0.131 mg (5% excess)
Lactose ** (particles): 91.869 mg
Sodium Starch Glycolate: 5 mg
Magnesium Stearate: 1 mg
Talc Silicified ***: 2 mg
* Corresponds to 0.112 mg levothyroxine sodium
** Consists of:
60.614 mg lactose H2O
0.505 mg gelatine and
30.75 mg starch maize
*** Consists of:
0.667 mg talc purified
1.333 mg colloidal silicon dioxide

Example 7

Dry powder comprising thyroid hormone (same composition as T4-100) was prepared.
Composition of 100 mg of dry powder:
Levothyroxine sodium hydrate *: 0.117 mg (5% excess)
Lactose ** (particles): 91.883 mg
Sodium Starch Glycolate: 5 mg
Magnesium Stearate: 1 mg
Talc Silicified ***: 2 mg
* Corresponds to 0.1 mg levothyroxine sodium
** Consists of:
60.628 mg lactose H2O
0.505 mg gelatine and
30.75 mg starch maize
*** Consists of:
0.667 mg talc purified
1.333 mg colloidal silicon dioxide

Example 8

Dry powder comprising thyroid hormone (same composition as T4-88) was prepared.
   Composition of 100 mg of dry powder:
   Levothyroxine sodium hydrate *: 0.103 mg (5% excess)
   Lactose ** (particles): 91.897 mg
   Sodium Starch Glycolate: 5 mg
   Magnesium Stearate: 1 mg
   Talc Silicified ***: 2 mg
   * Corresponds to 0.088 mg levothyroxine sodium
   ** Consists of:
   60.642 mg lactose H2O
   0.505 mg gelatine and
   30.75 mg starch maize
   *** Consists of:
   0.667 mg talc purified
   1.333 mg colloidal silicon dioxide

Example 9

Dry powder comprising thyroid hormone (same composition as T4-75) was prepared.
   Composition of 100 mg of dry powder:
   Levothyroxine sodium hydrate *: 0.087 mg (5% excess)
   Lactose ** (particles): 91.913 mg
   Sodium Starch Glycolate: 5 mg
   Magnesium Stearate: 1 mg
   Talc Silicified ***: 2 mg
   * Corresponds to 0.075 mg levothyroxine sodium
   ** Consists of:
   60.658 mg lactose H2O
   0.505 mg gelatine and
   30.75 mg starch maize
   *** Consists of:
   0.667 mg talc purified
   1.333 mg colloidal silicon dioxide

Example 10

Dry powder comprising thyroid hormone (same composition as T4-50) was prepared.
   Composition of 100 mg of dry powder:
   Levothyroxine sodium hydrate *: 0.058 mg (5% excess)
   Lactose ** (particles): 91.942 mg
   Sodium Starch Glycolate: 5 mg
   Magnesium Stearate: 1 mg
   Talc Silicified ***: 2 mg
   * Corresponds to 0.05 mg levothyroxine sodium
   ** Consists of:
   60.687 mg lactose H2O
   0.505 mg gelatine and
   30.75 mg starch maize
   *** Consists of:
   0.667 mg talc purified
   1.333 mg colloidal silicon dioxide

Example 11

Dry powder comprising thyroid hormone (same composition as T4-25) was prepared.
   Composition of 100 mg of dry powder:
   Levothyroxine sodium hydrate *: 0.029 mg (5% excess)
   Lactose **: 91.971 mg
   Sodium Starch Glycolate: 5 mg
   Magnesium Stearate: 1 mg
   Talc Silicified ***: 2 mg
   * Corresponds to 0.025 mg levothyroxine sodium
   ** Consists of:
   60.716 mg lactose H2O
   0.505 mg gelatine and
   30.75 mg starch maize
   *** Consists of:
   0.667 mg talc purified
   1.333 mg colloidal silicon dioxide B) In the following examples 12-13 the dry powder compositions of thyroid hormones are identical with composition the tablets of examples 1-2 of the patent document U.S. Pat. No. 6,646,007 B1, herein fully incorporated by reference.

Example 12

Dry powder comprising thyroid hormone (same composition as in example 1 of U.S. Pat. No. 6,646,007 B1, herein fully incorporated by reference) was prepared.
   Composition of dry powder:
   Levothyroxine sodium: 0.21 kg (+5% in excess)
   Lactose monohydrate: 131.8 kg
   Maize Starch: 50 kg
   Gelatin: 10 kg
   Croscarmellose sodium: 7 kg
   Magnesium stearate: 1 kg

Example 13

Dry powder comprising thyroid hormone (same composition as in example 2 of U.S. Pat. No. 6,646,007 B1, herein fully incorporated by reference) was prepared.
   Composition of 100 mg dry powder:
   Levothyroxine sodium: 0.1 mg
   Lactose monohydrate: 65.9 mg
   Maize Starch: 25 mg
   Gelatin: 5 mg
   Croscarmellose sodium: 3.5 mg
   Magnesium stearate: 0.5 mg C) In the following example 14 the dry powder composition of thyroid hormone is identical with the composition of the tablets of the example 1 of the patent document US-A1-2004/0033259, herein fully incorporated by reference.

Example 14

Dry powder comprising thyroid hormone (same composition as in example 1 of US-A1-2004/0033259, herein fully incorporated by reference) was prepared.
   Composition of 0.0334% levothyroxine sodium granulation intermediate:
   levothyroxine sodium: 567.2 mg
   Mannitol: 723.4 g
   Sucrose: 425 g
   Microcrystaline cellulose: 517 g
   Polyvinylpyrrolidone K30: 34 g
   Purified water: 165 g
   Ethanol 200 proof: 165 g
   Magnesium stearate: 1 kg
   Composition of dry powder (before drying):
   0.0334% levothyroxine sodium granulation intermediate: 1125 g
   Colloidal silicon dioxide: 5.3 g
   Magnesium stearate/Sodium lauryl sulfate 94/6: 30 g
   FD&C Yellow Aluminium Lake no. 6: 4.5 g
   Microcrystalline cellulose 136.5 g
   Mannitol: 648.8 g D) The inhaler of GSK as described in the document US-A-65553987—herein fully incorporated by reference—is used in all 14 examples above.

Test have shown that not only the inhaler (GSK product) keeps all its advantages (bridging of powder avoided, minimum of powder waste, maximum of useful life of device, accurate delivery of less flowable powders thus allowing the use of powder blends with reduced course excipient to drug ratios, hormone metered being constant regardless the number the auger is rotated after the appropriate dose has been metered, even dosing etc.) but also that the absorption of the stable thyroid hormone powder is improved, the dose being very accurately administrated and absorbed avoiding over/under-dosing.

All patients preferred the new administration way by inhalation as being easy and comfortable.

The invention claimed is:

1. A device comprising an inhaler suitable for administration of a stable dry powder blend, said device containing a blend comprising
   a) levothyroxine sodium hydrate,
   b) lactose particles, comprising lactose $H_2O$, gelatine and starch maize,
   c) sodium starch glycolate,
   d) magnesium stearate, and
   e) talc silicified, comprising talc purified and colloidal silicon dioxide;
and wherein the dry powder comprises levothyroxine sodium in an amount 4 to 0.02 mg per 100 mg of the dry powder.

2. The device according to claim 1 wherein the dry powder comprises lactose in an amount higher than 90 mg per 100 mg of the dry powder preparation.

3. The device according to claim 1 wherein the dry powder comprises lactose particles consisting of lactose $H_2O$, gelatine and starch maize, wherein the ratio by weight-mg of:
   "lactose $H_2O$":"gelatine":"starch maize" is 55-75:0.20-0.80:20-40.

4. The device according to claim 1 wherein the dry powder comprises sodium starch glycolate in an amount of 4-8 mg per 100 mg of dry powder.

5. The device according to claim 1 wherein the dry powder comprises magnesium stearatein an amount of 0.5-2 mg per 100 mg of dry powder.

6. The device according to claim 1 wherein the dry powder comprises talc silicified, in an amount of 2 mg per 100 mg of dry powder, wherein said talc silicified comprises talc purified and colloidal silicon dioxide in an amount of 0.667 mg of talc purified and 1.333 mg of colloidal silicon dioxide for 2 mg of talc silicified.

7. The device according to claim 1, wherein the blend further comprises a lake.

8. The device according to claim 1 wherein the dry powder comprises sodium starch glycolate in an amount of 5-6 mg per 100 mg of dry powder.

9. The device according to claim 1 wherein the dry powder comprises magnesium stearate in an amount of 1 mg per 100 mg of dry powder.

* * * * *